United States Patent [19]

Nielsen

[11] 4,170,706
[45] Oct. 9, 1979

[54] METHOD FOR PREPARING THE BISPICRATE SALT OF 2,3,7,8-TETRAAZASPIRO[4.4]NONANE

[75] Inventor: Arnold T. Nielsen, China Lake, Calif.

[73] Assignee: The United States of America as represented by the Secretary of the Navy, Washington, D.C.

[21] Appl. No.: 937,635

[22] Filed: Aug. 28, 1978

Related U.S. Application Data

[62] Division of Ser. No. 829,761, Sep. 1, 1977, Pat. No. 4,125,728, which is a division of Ser. No. 743,723, Nov. 22, 1976, Pat. No. 4,066,833.

[51] Int. Cl.² .............................................. C07D 487/10
[52] U.S. Cl. ..................................................... 548/356
[58] Field of Search ........................ 548/356; 568/710

[56] References Cited

PUBLICATIONS

Auwers et al., Chem. Ber. 1936, vol. 69, pp. 2347–2351.
Wertheim, Textbook of Organic Chemistry, Blakiston, N.Y., 1951, p. 568.

*Primary Examiner*—Alan L. Rotman
*Assistant Examiner*—Natalia Harkaway
*Attorney, Agent, or Firm*—R. S. Sciascia; W. Thom Skeer; L. E. K. Pohl

[57] ABSTRACT

Synthetic routes to 2,3,7,8-tetraazaspiro[4.4]nonane, its bispicrate salt, 2,3,7,8-tetraazaspiro[4.4]nona-2,7-diene, and 3,8-dicarbomethoxy-2,3,7,8-tetraazaspiro[4.4]nona-1,6-diene. The compounds are useful as high density fuels.

2 Claims, No Drawings

METHOD FOR PREPARING THE BISPICRATE SALT OF 2,3,7,8-TETRAAZASPIRO[4.4]NONANE

This is a division of application Ser. No. 829,761, filed Sept. 1, 1977, which has matured into U.S. Pat. No. 4,125,728. Ser. No. 829,761 was a division of application Ser. No. 743,723, filed Nov. 22, 1976, which has matured into U.S. Pat. No. 4,066,833.

BACKGROUND OF THE INVENTION

1. Field of the Invention

This invention relates to the compound 2,3,7,8-tetraazaspiro[4.4]nonane to 2,3,7,8-tetraazaspiro[4.4]nona-2,7-diene and to other derivatives of the nonane and to their preparation.

2. Description of the Prior Art

With the advent of oil shortages throughout the world, considerable interest has developed in the preparation of materials which are suitable for use as fuels and which are not derived from petroleum products. The present invention is one result of such interest.

Insofar as is known by the inventor, none of the claimed compounds were ever prepared prior to his preparation thereof. In fact, only a few routes leading to spiranes with two or more hydrazino or azo groups were previously described and these led to substituted derivatives which were not readily adaptable to the synthesis of the parent unsubstituted compounds.

SUMMARY OF THE INVENTION

According to this invention, 2,3,7,8-tetraazaspiro[4.4]nonane is prepared by the steps of (1) reacting a solution of 4-phenylurazole with a solution of potassium ethoxide and pentaerythrityl tetrabromide to form 2,2'-diphenyl-1,1',3,3'-tetraoxo-6,6'-spirobi[hexahydropyrazolo[1,2-a]-s-triazole], (2) reacting the s-triazole with sodium hydroxide and concentrated hydrochloric acid successively to form 2,3,7,8-tetraazaspiro[4.4]nonane bishydrochloride, (3) reacting the bishydrochloride with potassium bisulfate to form 2,3,7,8-tetraazaspiro[4.4]nonane sulfate and (4) reacting the sulfate with ammonia to prepare the nonane. Reaction of the nonane with mecuric oxide causes the diene, 2,3,7,8-tetraaspiro[4.4]nona-2,7-diene to form. Certain other derivatives of the nonane (in addition to the diene) are also prepared using hereinafter described techniques.

DESCRIPTION OF THE PREFERRED EMBODIMENT

For the convenience of the reader, it might be well, at the outset, to set forth the structures of some of the compounds spoken of below.

4 Phenylurazole has the structure:

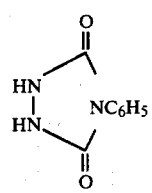

2,2'-Diphenyl-1,1',3,3'-tetraoxo-6,6'-spirobi[hexahydropyrazolo[1,2-a]-s-triazole], has the structure:

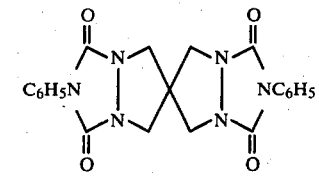

2,3,7,8-Tetraazaspiro[4.4]nonane has the structure:

2,3,7,8-Tetraazaspiro[4.4]nonane bishydrochloride has a structure which may be represented by:

2,3,7,8-Tetraazaspiro[4.4]nonane sulfate has a structure which may be represented by:

2,7-Bis(phenylcarbamoyl)-2,3,7,8-tetraazaspiro[4.4]nonane may be represented by:

3,8-Dicarbomethoxy-2,3,7,8-tetraazaspiro 4,4 nona-1,6-diene has the structure:

2,3,7,8-Tetraazaspiro[4.4]nona-2,7-diene has the structure:

The reactions utilized in preparing 2,3,7,8-tetraazaspiro[4,4]nonane, 2,3,7,8-tetraazaspiro 4,4 nona-2,7-diene and other derivatives of the nonane contemplated by this invention may be conveniently set forth by a plurality of examples.

EXAMPLE 1

Methyl 3-(phenylcarbamoyl)carbazate

A solution of methyl carbazate (91.9 g, 1.02 moles) in 450 ml of benzene was added dropwise with stirring during 45 min. to phenyl isocyanate (122 g. 1.02 moles); a temperature rise to near 80° C. was observed. After addition of the ester solution the mixture was heated under reflux, with stirring, for 45 min. Stirring was continued at ambient temperature for 15 hr. Removal of volatiles under reduced pressure gave 210.6 g (99%) of product ester, as long prisms, m.p. 154°–155°. Recrystallization from isopropyl alcohol/ethanol (4/1) gave a polymorph as chunky crystals, m.p. 166°–168°.

Anal. Calcd. for $C_9H_{11}N_3O_3$: C, 51.67; H, 5.30; N, 20.09. Found: C, 51.54; H, 5.45; N, 20.03.

4-Phenylurazole

A mixture of methyl 3-(phenylcarbamoyl) carbazate (209.2 g, 1.0 mole), 4 N aqueous potassium hydroxide solution (500 ml, 2.0 moles) and 100 ml of ethanol was heated with stirring under reflux for 5.5 hr. The mixture was then chilled and the chilled mixture treated with 12 N hydrochloric acid (170 ml) to adjust the solution to pH 1 and precipitate the product. The mixture was filtered and the solid product washed with water. The dried solid was extracted with 1300 ml of boiling ethanol and filtered hot to remove some insoluble material. Concentration of the filtrate to dryness gave 146.4 g of 4-phenylurazole, m.p. 208°–210°; a second crop was isolated from the aqueous filtrate, 7.4 g, m.p. 208°–210°; total yield 153.8 g (87%).

EXAMPLE 3

2,2'-Diphenyl-1,1',3,3'-tetraoxo-6,6'-spirobi[hexahydropyrazolo[1,2-a]-s-triazole]

To 4-phenylurazole (53.1 g, 0.3 mole) in 700 ml of absolute ethanol was added an ethanolic solution of potassium ethoxide, prepared from potassium (23.5 g, 0.6 mole) and 300 ml of absolute ethanol (calcium chloride tube attached). After warming on the steam bath for one hr. the solution was concentrated to dryness. The residue was treated with dry dimethylformamide (1 liter) and the mixture distilled until the still head temperature reached 135° C. (9 ml of distillate removed). A solution of pentaerythrityl tetrabromide (58.2 g, 0.15 mole) in 250 ml of warm, dry dimethylformamide was placed in a heated dropping funnel (wrapped with heating tape) maintained sufficiently warm to keep the solid in solution. This warm solution was added dropwise to the refluxing, stirred reaction mixture during 8 hr; heating at reflux and stirring were continued for an additional 14 hr. The reaction mixture was then chilled in an ice bath and the precipitated potassium bromide removed by filtration. After washing the precipitate with dimethylformamide the filtrate was concentrated to near dryness under reduced pressure while heating on the steam bath. Water (1 l) was added to the residue and the mixture warmed on the steam bath. The water layer was removed by decantation and the residue triturated with water and the washings discarded. The residue was digested with 200 ml of boiling ethanol; after cooling, filtering and washing the residual product with ethanol there was obtained 23.4 g of crude triazole, m.p. 325°–335°; this material was digested with 500 ml of boiling ethanol for 1.5 hr. and filtered hot to yield 16.0 g of the triazole, m.p. 336°–345° (an additional 0.6 g, m.p. 341°–348°, was isolated from the filtrates, total yield 16.6 g, 26%); recrystallization from boiling dimethylformamide yields tiny prisms, m.p. 349°–350° (55% recovery). Parallel runs gave comparable results.

Calcd. for $C_{21}H_{18}N_6O_4$: C, 60.28; H, 4.34; N, 20.09, mol. wt. 418.4. Found: C, 60.29; H, 4.49; N, 20.08, mol. wt. 423 (dimethylformamide).

Pentaerythritol tetrabenzenesulfonate was substituted for pentaerythrityl tetrabromide in one run using the above procedure to provide a 16% yield of the triazole.

EXAMPLE 4

2,3,7,8-Tetraazaspiro[4.4]nonane bishydrochloride

A mixture of triazole from Example 3 (16.75 g, 0.040 mole), sodium hydroxide (40 g, 1.0 mole) and 400 ml of oxygen-free 95% ethanol (degassed by bubbling in oxygen-free nitrogen) was heated under reflux in an oxygen-free nitrogen atmosphere with stirring (magnetic) for 48 hr. The mixture, after chilling to 0° C. for 1 hr. was filtered by suction and the solid washed with oxygen-free ethanol. The filtrate was immediately acidified to pH 1 by adding concentrated hydrochloric acid (80 ml) and concentrated to dryness under reduced pressure on the steam bath. Water (130 ml) was added to the residue to dissolve all but ca. 0.5 g of dark gummy material. The solution was filtered by suction and the solid washed with water. Aqueous sodium hydroxide solution (50 ml of 20%) was added to make the solution alkaline (pH 12, nitrogen atmosphere maintained) and the solution extracted three times with ether (50 ml portions); the extracts were dried and concentrated to yield 6.0 g (30%) of aniline.

The aqueous alkaline solution remaining from the ether extraction was immediately acidified to pH 1 with concentrated hydrochloride acid (15 ml). After filtration to remove traces of gummy material the filtrate was concentrated to dryness under reduced pressure. Concentrated hydrochloric acid (150 ml) was added to the residue and the mixture stirred magnetically for 1 hr. at 60°–90° (water bath temperature). After cooling, the mixture was filtered through a sintered glass filter to remove sodium chloride and washed with concentrated hydrochloric acid. Concentration of the filtate to dryness gave a gummy residue (10.0 g) which was redissolved in 75 ml of hot concentrated hydrochloric acid and cooled to 25° to deposit more sodium chloride (0.7 g removed by filtration and washed with concentrated hydrochloric acid). The filtrate (ca. 100 ml) was chilled to 0° and seeded to yield, in successive crops, 5.63 g (70%) of dihydrochloride, m.p. 192°–200°; recrystallization from concentrated hydrochloric acid, followed by drying in air at 25°, gave crystals, m.p. 208°–210° without decomposition (on cooling to 140° the material recrystallized as long needles, m.p. 150°–155°); ir (potassium bromide): 3170 $cm^{-1}$ (NH); nmr (deuterium oxide): δ3.58 (s, 8, $CH_2$).

Anal. Calcd. for $C_5H_{14}Cl_2N_4$: C, 29.86; H, 7.02; Cl, 35.26; N, 27.86; Found: C, 29.76; H, 7.03; Cl, 35.46; N, 27.89.

EXAMPLE 5

2,3,7,8-Tetraazaspiro[4.4]nonane sulfate

Ion exchange resin, polystyrene quaternary ammonium chloride type (Biorad AG1X-10, 200–400 mesh, 150 g), was thoroughly exchanged with aqueous saturated potassium bisulfate solution until tests for chloride ion were negative. To this bisulfate resin in a column was introduced a solution of 2.50 g of bishydrochloride from Example 4 in 20 ml of water. Concentration of the eluate to dryness gave 2.8 g of crystalline solid which was dissolved in water (10 ml) and diluted with 60 ml of ethanol to precipitate the sulfate salt after chilling at 0°. The crystals were filtered and washed with ethanol to yield 2.51 g (89%) of the sulfate, as small prisms, m.p. 231°-234° (dec.)

Anal. Calcd. for $C_5H_{14}N_4O_4S$: C, 26.54; H, 6.24; N, 24.76, S, 14.17. Found: C, 26.53; H, 6,25; N, 24.73; S, 14.24.

EXAMPLE 6

2,3,7,8-Tetraazaspiro[4.4]nonane

The sulfate salt from Example 5 (4.0 g) was placed in a 3-necked flask flushed with oxygen-free dry nitrogen and equipped with a dry-ice-acetone condenser, ascarite tube and magnetic stirrer and surrounded by a dry-ice acetone cold bath. Ammonia (100 ml) was condensed into the apparatus during 3 hr. with stirring. The ammonia inlet was replaced by oxygen-free dry nitrogen and the cold bath was removed. The ammonia was allowed to evaporate completely at ambient temperature with stirring. To the residue was added 50 ml of oxygen-free absolute ethanol (degassed by passing through oxygen-free nitrogen) and the mixture stirred at ambient temperature for 3 hr. The mixture was filtered (to remove ammonium sulfate) into a distilling flask equipped with an oxygen-free nitrogen capillary inlet. Solvents were removed at 30 mm pressure keeping the bath temperature below 50. A white solid precipitates from the ethanol solution as the distillation proceeds; after all solvents were removed there remained 2.17 g (95%) of the amine (the nonane), clusters of flat waxy crystals, m.p. 140°-170° (open or sealed capillary, slow heating from bath temperature 25°), m.p. 180°-190° (open capillary, rapid heating from bath temperature 150°; a clear liquid resulted on melting with no gassing and on cooling the sample recrystallized; $d_4^{25}$ 1.21 (compression at 40,000 psi; ir (potassium bromide): 3400, 3200 cm$^{-1}$ (NH); nmr (deuterium oxide): δ, 3.0 (s, 8, CH$_2$), 4.78 (s,4, OH from KH exchange).

Anal. Calcd. for $C_5H_{12}N_4$: C, 46.85; H, 9.44; N, 43.71; mol. wt. 128.2. Found: C, 46.63; H, 9.19; N, 43.47; mol. wt. 128 (mass spec), 132 (osmometry, dimethylformamide).

EXAMPLE 7

A bispicrate salt was prepared by reaction of 0.128 g (1.0 mmole) of the nonane of Example 6 with picric acid (0.458 g, 2.0 mmole) in 5 ml of oxygen-free warm ethanol to yield 0.49 g (84%) of the picrate salt after crystallization from 50% aqueous ethanol, m.p. 182°-184°. Recrystallization gave rectangular yellow prisms, m.p. 185°-186° (dec.)

Anal. Calcd. for $C_{17}H_{18}N_{10}O_4$: C, 34.82; H, 3.09; H, 23.89. Found: C, 35.06; H, 2.96; N, 24.02.

EXAMPLE 8

2,7-Bis(phenylcarbamoyl)-2,3,7,8-tetraazaspiro[4.4]nonane

A mixture of the triazole from Example 3 (1.77 g, 4.1 mmole), sodium hydroxide (3.2 g, 80 mmole) and 50 ml of methanol was heated under reflux (nitrogen atmosphere) for 24 hr. After chilling at 0° the mixture was filtered and the solid washed with methanol. The solid was treated with dilute hydrochloric acid to dissolve the sodium carbonate present leaving the product which was filtered off and washed with water to yield 0.77 g (52%) of 2,7-bis(phenylcarbamoyl)-2,3,7,8-tetraazaspiro[4.4]nonane, m.p. 227°; recrystallization from ethanol gave long prisms; m.p. 230°-231°; ir (potassium bromide): 3330, 3230 cm$^{-1}$ (NH), 1660 (C=O); nmr (dimethyl sulfoxide-d$_6$): δ 9.0 (s, 2, NHCO; signal disappears on addition of deuterium oxide), 6.8-7.8 (m, 10, C$_6$H$_6$), 5.67, 5.80 (d,d, J=9.7, 8.2 Hz, 2 CH$_2$NH; signals disappear on addition of deuterium oxide), 3.57 (broad singlet, 4, CH$_2$NCO; on addition of deuterium oxide the signal shifts to 3.72δ), 2.97, 3.00 (doublets, J=9.7, 8.2 Hz, respectively, 4, CH$_2$NH; signal becomes a singlet on addition of deuterium oxide, 2.92δ).

Anal. Calcd. for $C_{19}H_{22}N_6O_2$: C, 62.28; H, 6.05; N, 22.94; mol. wt. 366.4. Found: C, 62.80; H, 6.38; H, 23.23; mol. wt. 325 (dimethylformamide).

The methanolic filtrate remaining from removal of the product and sodium carbonate was acidified with concentrated hydrochloric acid to pH 1. The filtrate was concentrated to dryness, triturated with methanol (25 ml) and filtered to remove sodium chloride. The filtrate was concentrated to dryness and dissolved in 2 ml of water and made basic with 10% aqueous sodium hydroxide solution. The resulting mixture was extracted with ether and the extracts dried with magnesium sulfate; removal of solvent under reduced pressure gave aniline, 0.26 g (35%); its benzoyl derivative was prepared. m.p. 163°-165°. Some Example 7 picrate, m.p. 174°-178° was also ultimately isolated from the reaction mixture.

EXAMPLE 9

3,8-Dicarbomethoxy-2,3,7,8-tetraazaspiro[4.4]nona-1,6-diene

To a solution of spirononane from Example 6 (0.64 g, 5 mmole) in 20 ml of oxygen-free ethanol was added sodium carbonate (0.56 g, 10.6 mmole) and, during 2 min., methyl chloroformate (1.0 g, 10.6 mmole). The mixture was heated under reflux (oxygen-free nitrogen atmosphere) with stirring for 2.5 hr. The mixture was concentrated to dryness, the residue extracted with boiling 2-propanol and filtered hot to remove sodium chloride. Concentration of the filtrate to dryness gave 1.17 g of gum which was crystallized from 2-propanol to yield the compound of this example (0.11 g, 9%, m.p. 185°-190°); recrystallization from 2-propanol gave small crystals, m.p. 195°-197°; ir (potassium bromide): 1720 cm$^{-1}$ (C=O), 1590 (C=N); nmr (deuteriochloroform): δ7.10 (s, 2, CH=), 4.20 (q, 4, CH$_2$), 4.10 (s, 6, CH$_3$).

Anal. Calcd. for $C_9H_{12}N_4O_4$: C, 45.00; H, 5.04; N, 23.33; mol. wt. 240.22 Found: C, 44.84; H, 4.88; N, 23.32; mol. wt. 235.

EXAMPLE 10

2,3,7,8-Tetraazaspiro[4.4]-nona-2,7-diene

A mixture of spirononane from Example 6 (0.64 g, 5 mole), mercuric oxide (2.17 g, 10 mmole) and ether (50 ml) was stirred magnetically at ambient temperature in a nitrogen atmosphere (oxygen not rigorously excluded) for 11 hr. The mixture was filtered to remove a gray solid, and the filtrate concentrated to yield 0.52 g of the diene, as needle-shaped prisms (m.p. 125°-137°, Kofler, with change to rosettes near 110°; m.p. 122°-125° in open capillary to clear liquid with previous sintering near 110°, followed by slow gas evolution at 150°–220° and rapid gas evolution at 220°). Recrystallization from cyclohexane gave feathery prisms, m.p. 113°–119° (capillary). The gray solid containing mercury was extracted with warm 2-propanol and filtered; concentration of the extracts gave additional diene, 0.10 g, m.p. 100°–101° (capillary), having an infrared spectrum identical to the principal fraction; total yield 0.62 g (100%); $d_4^{25}$ 1.26 (pressed pellet at 40,000 psi); ir (potassium bromide): 1520 cm$^{-1}$ (N=N); NH bands absent; nmr (deuteriochloroform): $\delta$, 4.62 (s, 8, CH$_2$); on standing a small singlet appears at $\delta$ 7.57 (CH=).

Anal. Calcd. for $C_5H_8N_4$: C, 48.37; H, 6.50; N, 45.13; mol. wt. 124.15. Found: C, 48.57; H, 6.74; N, 45.34; mol. wt. 124 (mass spec); 130 (osmometry, chloroform).

2,3,7,8-Tetraazaspiro[4.4]nonane and its derivative 2,3,7,8-tetraazaspiro[4.4]nona-2,7-diene are hypergolic with fuming nitric acid. Additionally, they have high densities (greater than 1.2). Accordingly they are useful as fuels.

All temperatures used herein are in ° C.

What is claimed is:

1. A method for preparing the bispicrate salt of 2,3,7,8-tetrazaspiro[4.4]nonane comprising the steps of:
   A. preparing a solution of 4-phenylurazole in ethanolic potassium ethoxide and a solution of pentaerythrityl tetrabromide in dimethylformamide, forming a reaction mixture from the two solutions, reacting it to cause 2,2-diphenyl-1,1',3,3'-tetraoxo-6,6'-spirobi[hexahydropyrazolo[1,2-a]-s-triazole] to be formed and recovering the s-triazole;
   B. reacting the s-triazole with sodium hydroxide and hydrochloric acid in succession to form 2,3,7,8-tetraazaspiro[4.4]nonane bishydrochloride and recovering the bishydrochloride;
   C. Reacting the bishydrochloride with potassium bisulfate to form 2,3,4,8-tetrazaspiro[4.4]nonane sulfate and recovering the sulfate;
   D. subjecting the sulfate to ammonia to form 2,3,7,8-tetraazaspiro[4.4]nonane; and
   E. reacting the nonane with picric acid.

2. A method according to claim 1 wherein the reaction of step E is carried out in the presence of ethanol.